(12) United States Patent
Li

(10) Patent No.: US 11,020,055 B1
(45) Date of Patent: Jun. 1, 2021

(54) INTELLIGENT MULTIFUNCTION BED MONITOR

(71) Applicant: Edward Li, San Diego, CA (US)

(72) Inventor: Edward Li, San Diego, CA (US)

( * ) Notice: Subject to any disclaimer, the term of this patent is extended or adjusted under 35 U.S.C. 154(b) by 0 days.

(21) Appl. No.: 16/906,633

(22) Filed: Jun. 19, 2020

(51) Int. Cl.
*A61B 5/11* (2006.01)
*A61G 7/05* (2006.01)
*A61B 5/00* (2006.01)
*H01Q 1/22* (2006.01)

(52) U.S. Cl.
CPC .......... *A61B 5/6892* (2013.01); *A61B 5/1115* (2013.01); *A61B 5/746* (2013.01); *A61G 7/05* (2013.01); *H01Q 1/2216* (2013.01); *A61G 2205/60* (2013.01)

(58) Field of Classification Search
CPC ... A61B 5/6891; A61B 5/6892; A61B 5/1115; A61G 2205/60
See application file for complete search history.

(56) References Cited

U.S. PATENT DOCUMENTS

| | | | |
|---|---|---|---|
| 6,025,782 A | 2/2000 | Newham | |
| 6,292,102 B1 | 9/2001 | Smith | |
| 6,417,777 B2 | 7/2002 | Fitzgerald et al. | |
| 6,778,090 B2 | 8/2004 | Newham | |
| 6,917,293 B2 | 7/2005 | Beggs | |
| 7,242,308 B2 | 7/2007 | Ulrich et al. | |
| 7,378,975 B1 | 5/2008 | Smith et al. | |
| 7,538,659 B2 | 5/2009 | Ulrich et al. | |
| 7,666,151 B2 | 2/2010 | Sullivan et al. | |
| 7,893,842 B2 | 2/2011 | Deutsch | |
| 7,940,187 B2 | 5/2011 | Newham | |
| 8,350,709 B2 | 1/2013 | Receveur | |
| 8,564,445 B2 | 10/2013 | Dring et al. | |
| 8,698,511 B2 | 4/2014 | Wendt et al. | |
| 8,752,220 B2 | 6/2014 | Soderberg et al. | |
| 8,766,804 B2 | 7/2014 | Reeder et al. | |
| 8,994,385 B2 | 3/2015 | Virnich et al. | |
| 9,000,331 B2 | 4/2015 | Virnich et al. | |
| 9,013,313 B2 | 4/2015 | Paine | |
| 9,061,641 B2 * | 6/2015 | Lamesch ................ B60N 2/002 |
| 9,132,850 B2 | 9/2015 | Virnich et al. | |

(Continued)

*Primary Examiner* — William J Levicky
*Assistant Examiner* — Nathan A Baldwin
(74) *Attorney, Agent, or Firm* — The Patent Shoppe; Patrick Lavender

(57) ABSTRACT

A system for monitoring the health and safety of recumbent individuals. In some embodiments, the bed monitor system comprises a wired or wireless sensor mat which may be positioned upon a bed mattress and underneath a bedsheet. Multiple RFID tag sensors embedded within the sensor mat can detect physical, bodily, and environmental attributes and transmit this information to a controller box for further processing. Turn regiment, prohibited body positions, imminent fall danger, and bed occupancy may therefore be tracked and updated accordingly. In some embodiments, the system can dynamically generate positional images of a body proximate to the sensor mat in order to identify adverse conditions requiring attention. Incontinence discharges can also be detected by sensors and algorithms which can differentiate urinary from fecal incontinence events. Various embodiments of the system are portable, allowing for a rapid set-up within hospital venues and within other care facilities.

13 Claims, 11 Drawing Sheets

| Sensing-tracking Function | Main Detection Technology | Confirming Detection Technology | Alarm Discrimination Techniques |
|---|---|---|---|
| 1. Body position | RFID Moisture Sensor | RFID Temperature Sensor | Amplitude, spatial, temporal, pattern, AI |
| 2. Fall | RFID Moisture Sensor | RFID Temperature Sensor | Amplitude, spatial, temporal, pattern, AI |
| Bed Vacancy | RFID Moisture Sensor | RFID Temperature Sensor | Amplitude, spatial, temporal, pattern, AI |
| 3. Incontinence, Urine | RFID Moisture Sensor | RFID Temperature Sensor | Amplitude, spatial, temporal, pattern, AI |
| " Stool | H₂S Gas Sensor | RFID Moisture Sensor | Amplitude, spatial, temporal, pattern, AI |

(56) References Cited

U.S. PATENT DOCUMENTS

| | | | |
|---|---|---|---|
| 9,152,768 B2 | 10/2015 | Ribble | |
| 9,311,540 B2 | 4/2016 | Ecker et al. | |
| 9,649,230 B1 | 5/2017 | Li | |
| 9,764,668 B2 | 9/2017 | Lamesch et al. | |
| 9,814,410 B2 | 11/2017 | Kostic et al. | |
| 10,054,479 B2 | 8/2018 | Nachtigal et al. | |
| 10,126,149 B2 | 11/2018 | Virnich et al. | |
| 10,176,297 B2 | 1/2019 | Zerhusen et al. | |
| 10,206,630 B2 | 2/2019 | Stone et al. | |
| 10,231,647 B2 | 3/2019 | Kostic et al. | |
| 10,251,793 B1 | 4/2019 | Li | |
| 10,478,359 B2 | 11/2019 | Kostic et al. | |
| 2010/0290503 A1* | 11/2010 | Rumpf, Jr. | G01K 7/32 374/163 |
| 2014/0343889 A1* | 11/2014 | Ben Shalom | A61G 7/057 702/139 |
| 2017/0245799 A1* | 8/2017 | Fleischer | A61B 5/6807 |
| 2017/0325683 A1* | 11/2017 | Larson | A61B 5/447 |
| 2018/0021184 A1* | 1/2018 | Monson | A61B 5/6804 340/573.5 |

\* cited by examiner

FIG. 9

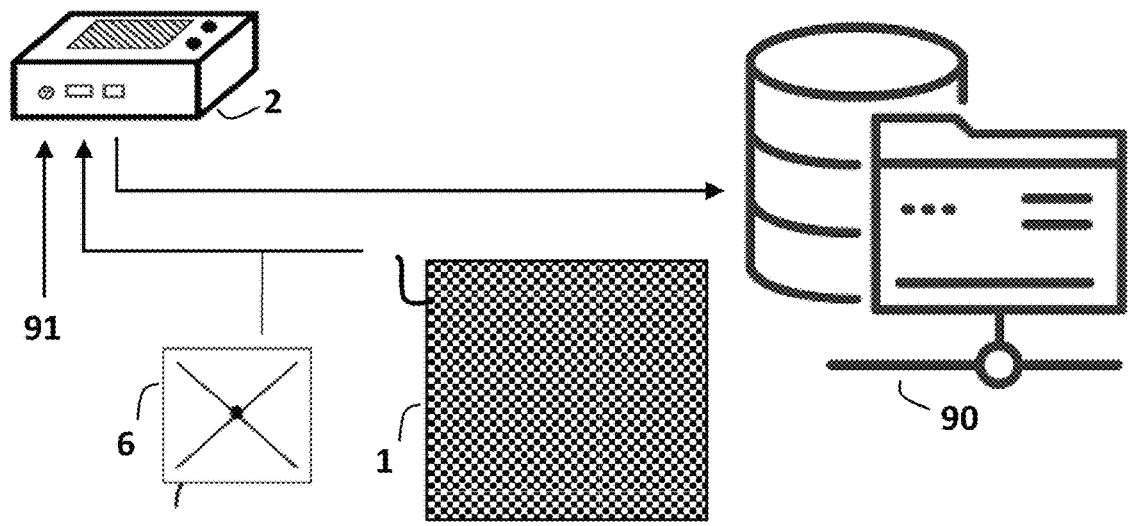

FIG. 10

| Sensing-tracking Function | | Main Detection Technology | Confirming Detection Technology | Alarm Discrimination Techniques |
|---|---|---|---|---|
| 1. | Body position | RFID Moisture Sensor | RFID Temperature Sensor | Amplitude, spatial, temporal, pattern, AI |
| 2. | Fall | RFID Moisture Sensor | RFID Temperature Sensor | Amplitude, spatial, temporal, pattern, AI |
|  | Bed Vacancy | RFID Moisture Sensor | RFID Temperature Sensor | Amplitude, spatial, temporal, pattern, AI |
| 3. | Incontinence, Urine | RFID Moisture Sensor | RFID Temperature Sensor | Amplitude, spatial, temporal, pattern, AI |
|  | " Stool | H₂S Gas Sensor | RFID Moisture Sensor | Amplitude, spatial, temporal, pattern, AI |

INTELLIGENT MULTIFUNCTION BED MONITOR

FIELD OF THE INVENTION

The present subject matter relates generally to the field of bed monitoring systems. More particularly, the present subject matter relates in one exemplary aspect to a hospital bed monitoring system which utilizes a plurality of embedded radio frequency identification tag sensors in a flexible mat installed below a bedsheet to detect patient body position, bed vacancy, and incontinence discharges.

BACKGROUND OF THE INVENTION

Patients in hospital intensive and acute care units (ICU/ACU), extended care facilities, nursing homes and home care need to be monitored for medical and safety reasons while in bed. Special monitoring is required for non-ambulatory patients who are clinically confined to their bed due to preexisting conditions or as a result of certain medical procedures.

Turn monitoring can be particularly important in patient health maintenance. Immobile patients need to be turned at prescribed intervals to avoid Decubitus ulcers, commonly called "bedsores," which occur in protruding anatomical pressure points and which are caused by prolonged stationary body positions. Pressure ulcers cost the U.S. health system $26.8 billion a year (Healthcare Finance News, Oct. 10, 2019). Hospital Acquired Pressure Ulcers (HAPU) is a concern for all bedbound patients. HAPU incidents were 9% among older hospitalized patients ("Incidence of HAPU", PLOS ONE Journal 0227052, 2018). 11% of nursing home patients suffer from pressure sores, according to a 2009 study (NCHS Data Brief, number 14). Florence Nightingale wrote in 1859 that "If he [the patient] has a bedsore, it's not the fault of the disease, but of the nursing."

Traditionally, body position has not been monitored when it comes to mitigating pressure sores in care facilities. Rather, caregivers would attempt to turn immobile patients at Industry recommended 2-hour intervals. Some pitfalls of this approach include unnecessary care expenditures associated with scheduled turns. This is because a certain set of patients (for example, postoperative patients who are at least semi-mobile) may have already turned on their own volition prior to their next scheduled turn.

Failure to turn patients in a timely manner can also present health related issues. Importantly, depending on the staff ratio and the existing level of care provided at a given facility, turn schedules can be unintentionally delayed or skipped, which can cause irritation or exacerbation of pressure sores. The prevalence of pressure sores is often an indelible sign of patient care negligence, and hospitals, patients, patient relatives, and care evaluation agencies are often keenly aware of this metric.

There are other potential issues attendant to failing to track a patient's position in a hospital bed. For example, sometimes a patient will have sutures located on one side of his/her body, where such sutures should not be in contact with the mattress. There are also certain orthopedic procedures which require a patient to remain immobile in order to heal. Myriad other examples exist where it is possible for a patient to deviate from medically prescribed parameters.

Further, patients other than invalids in enhanced care facility beds are at risk of falling due to natural and habitual urges to get up. Fall prevention is one of the most important goals in all hospitals and care facilities. It is commonly accepted that "the responsibility for fall intervention has been placed squarely on the shoulders of nurses" (National Institutes of Health, PCM5371163, 2015, "The Safety of Hospital Beds"). Between 700,000 to 1 million hospitalized patients will fall each year ("Preventing Falls in Hospitals", Agency for Healthcare Research and Quality Publication No. 13-0015-EF, January 2013). The CDC reports that up to 70% of nursing home residents fall each year (June 2015 article "Nursing Home Falls"). Further, a 2014 report found that "nearly 10% of Medicare skilled nursing facility residents experienced a fall resulting in significant injury" (HHS February 2014. Report No. OEI-06-11-00370).

Aside from potentially adverse health consequences to patients, fall data can also define a hospital's public reputation. Trade and government ratings, not to mention potential legal and insurance consequences, can also be adversely affected.

Apart from these issues, incontinence conditions among bedbound patients also require special care. Medical care staff ordinarily treat bedbound patients as incontinent by virtue of the fact that they cannot leave the bed to attend to their needs. Timely absorbent pad changes can help mitigate Incontinence-Associated Dermatitis (IAD), commonly called "diaper rash," which can further lead to pressure ulcers and secondary skin infections. 78% of acute care hospital adult patients wearing diapers suffer from these conditions (US Department of Health and Human Services, Office of the Inspector General; February 2014. Report No. OEI-06-11-00370). Presently, flat absorbent underpads have largely replaced adult diapers, since underpads minimize skin contact with wastes that can cause IAD. Absorbent pads need to be monitored for incontinence events in order to facilitate timely pad changes. Currently, no incontinence monitor is known to be of widespread use in any hospital. The reason for this may be because conventional incontinence detection devices have been designed to be embedded or inserted into incontinence absorbent pads, requiring high costs in customized pads and/or extra cleaning and sanitizing in the case of insertable sensors.

What is needed is a bed monitoring system capable of detecting and distinguishing between types of incontinence events, an individual's current position and movement in a bed over a designated period of time, and whether the state of the bed is currently occupied or vacant. Such a system should be capable of remotely detecting incontinence on a generic, unaltered absorbent pad. What is also needed is a bed monitoring system which can further analyze a set of collected positional data recorded over a designated period in order to forecast that an individual is currently attempting to get out of bed and notify care personnel accordingly. Ideally, the system would be portable and allow for rapid set-up within hospital venues and other care facilities.

SUMMARY OF THE INVENTION

Briefly stated, in accordance with several embodiments, there is provided a sensor populated mat for monitoring various characteristics of an individual's health and safety. The mat may be placed on a mattress and underneath a bedsheet. In some embodiments, the bed monitor is a two-component system which includes a sensor embedded mat and a controller box. In some embodiments, the system can monitor patients (for example, bedbound, immobile, and/or semi-mobile patients) for conditions which may adversely affect patient health and safety if not attended to promptly. These conditions include, without limitation, prolonged sleep position, fall risks, bed vacancy and incontinence. Monitoring can be accomplished by sensors which do not need to be connected to or worn by the patient, but rather, positioned at a distance from the patient body. In some embodiments, the monitoring system is portable, enabling quick set-up at hospital venues and within other care facilities. The portable nature of the system enables the system to be redeployed to another bed when no longer needed by a corresponding patient. Alternatively, the system can follow a particular patient among different hospital units or health care facilities, retaining in memory information that is specific to that particular patient.

According to some embodiments, non-contact patient monitoring can be accomplished with a selection of RFID tag sensors encapsulated in the flexible sensor mat. The use of a single sensor can yield the presence and signal strength level of an attribute under detection. A plurality of sensors may be used to add spatial, temporal and pattern recognition capabilities. In this way, an image of a patient's body above the sensor mat can be assembled with suitably affected sensors—the bigger the sensor array, the higher the resolution. The resultant digital image may correspond to, for example, a composite coarse pixel picture. Signal strength reported by each sensor may correspond to the brightness of the equivalent pixel. An example is the added resolution of relative signal levels expected from the firmer contact from a host patient posterior versus the hollow of the back or waistline affecting moisture or temperature sensors. In some embodiments, a moving image, analogous to a cartoon, may also be available with added timing (i.e., temporal-based) data to enable activity pattern recognition. With a composite of moving images over time, a patient attempting to exit his or her hospital bed can be recognized as distinct pages of activity images which can be further refined with artificial intelligence (AI) algorithms using accumulated in-situ data.

According to some embodiments, bed vacancy may be identified when all sensors report null readings, as when the patient is off the bed without medical permission. An incontinent patient, most commonly wearing an open back hospital gown, is normally fitted with a generic absorbent article, either lying on an absorbent underpad or wearing a diaper. Since the absorbent article is on the bedsheet and in registration with the sensor mat, the type of incontinence (urine or feces) and its progress in real time can be detected and tracked using outputs from RFID tag moisture, temperature, and gas sensors. The volume of urine voiding can be determined by the spreading size of the wet spot on the absorbent article over time. An adjustable volume value may be used to determine a trigger level for a urine incontinence alarm. In this manner, the system can advantageously refrain from issuing an alarm upon detecting merely a small volume discharge which typically does not require an absorbent article change. In some embodiments, solid fecal incontinence may be distinguished by the presence of its characteristic Hydrogen Sulfide gas, detectable with one or more $H_2S$ gas sensors.

In one exemplary aspect, a bed monitoring system is disclosed. In one embodiment, the bed monitoring system includes a sensor mat which includes a plurality of RFID tags, wherein each RFID tag includes an integrated circuit and an internal antenna that is adapted to be resonant with an external signal source; and a plurality of sensors, wherein each sensor is communicatively coupled to an associated RFID tag of said plurality of RFID tags; and a controller box which includes a processor; a memory module communicatively coupled to the processor; and an RFID transceiver adapted to receive a set of sensory data from each sensor of the plurality of sensors; wherein each set of sensory data includes at least one of a moisture sensor reading, a temperature sensor reading, a pressure sensor reading and a gas sensor reading; and wherein the memory module includes a set of instructions which, when executed by the processor, generates a first set of data indicating locations where part of a human body is proximate to a sensor of the sensor mat, and a second set of data indicating locations where an incontinence discharge is proximate to a sensor of the sensor mat.

BRIEF DESCRIPTION OF THE DRAWINGS

FIG. 9 is a schematic of an exemplary bed monitoring system in relation to a Hospital Information System (HIS) according to an embodiment of the present invention.

FIG. 10 is a table summarizing a set of functions tracked by the sensor mat and the technologies involved in acquiring and analyzing sensed data for activating respective alarms according to an embodiment of the present invention.

DETAILED DESCRIPTION OF THE INVENTION

Figure 1A:
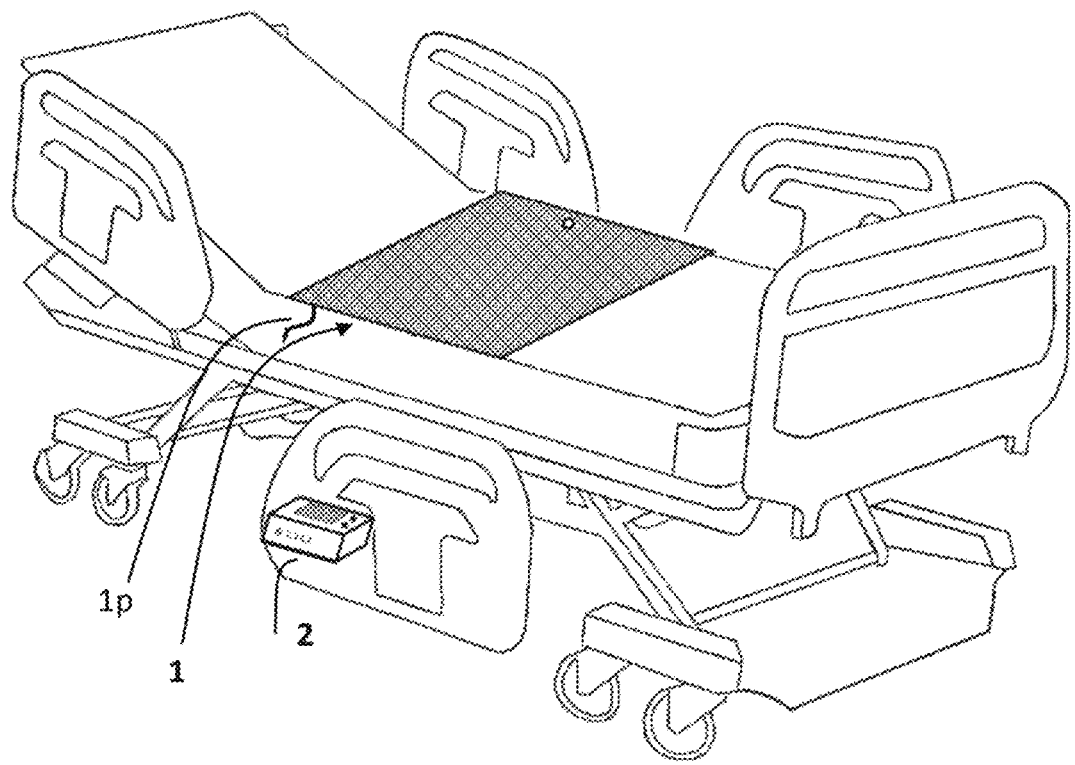
FIG. 1A is a perspective view of a bed monitoring system including a controller box and a sensor embedded mat positioned on a hospital bed mattress where the transceiver antenna(s) are integrated with the sensor mat, according to an embodiment of the present invention.

In the following description, reference is made to the accompanying drawings in which it is shown by way of illustration specific embodiments in which the invention can be practiced. It is to be understood that other embodiments can be used and structural changes can be made without departing from the scope of the embodiments of this invention.

Some embodiments include a portable multifunction hospital bed monitor with the following functions: (1) Sense and track patient body position; (2) Sense and track an impending patient fall; (3) Sense and track bed occupancy status; (4) Sense and track patient incontinence. The bed monitor may include a sensor populated flexible mat with multiple RFID tag sensors, and a custom controller box.

A radio communication link can be initiated when a transmitter sends a resonant frequency signal with coded information to a mating receiver. This is the basis for verifying the identity of an RFID tag, which in some cases, can be as small as an adhesive label. RFID tags are commonly used in security applications such as automated asset tracking, automated toll booths, secured turnstiles, and secured garages.

According to some embodiments, sensors can be utilized which use RFID technology for detecting physical or environmental attributes, including without limitation moisture, temperature, pressure, gas, and pH. In some embodiments, each attribute may be characteristically sensitive to a RF frequency. A high frequency radio signal is attenuated when it intersects with moisture. SAR (Synthetic Aperture Radar) used in Earth mapping for biomass is based on this principle. High Frequency (HF) and Ultra High Frequency (UHF) may be used as moisture detection probes. Currently, P band (0.3 to 1 GHz) or L band (1 to 2 GHz) radio frequencies are common in SAR mapping of Earth's biomass. A commercial microwave oven operates at 0.915 GHz while a home microwave oven uses 2.45 GHz, indicating that RF frequency in these same bands is absorbed readily by moisture in the materials these ovens are designed to cook. Commercial electromagnetic sensing VHF or UHF RFID moisture sensor tags using the same P or L bands are used extensively to detect rain leakages in auto door seals in one of the final quality check stages in car production. There are other types of RFID based moisture sensors that use the RFID tag as a medium for transmitting discrete sensor data. Either type can be used depending on design goals. The human body is 60% moisture, and responds well to UHF RFID moisture sensors.

In some embodiments, multiple arrayed RFID sensors can resolve body position, body absence (i.e., bed vacancy) and the occurrence of an incontinence event. In some embodiments, the sensors require no direct contact to a human body, i.e. they can detect the presence of a part of a human body that is proximate to a sensor. For example, in some embodiments, the sensors can detect the presence of a human body that is positioned within 5 cm of the sensor.

RFID tags can be active or passive according to various embodiments. Active tags need to be powered by an external electrical source such as a power supply or battery. Passive tags are not powered directly, but rather, are energized by an internal power source, most often an electronic capacitor which captures power derived when a tag receives resonant radio waves. There are advantages to active and passive tags depending on design and usage.

RFID tag sensors are commonly square or rectangular with a total area of one or two square inch(s) and about the thickness of a few sheets of printer paper. Its shape and size depend on antenna design, which in turn is dependent on application and frequency. The two main components of a RFID tag sensor are its antenna and integrated circuit (RFIC); the former is commonly a shaped conductive trace tuned to a special radio frequency range, the latter is a transceiver incorporating a processor, memory and radio frequency control circuitry. According to some embodiments, the rewritable memory in each RFIC may be used to record patient ID, medical information, as well as information needed to complete sensing and tracking functions. Information may be programmed into the RFID tag when it is in the range of an RFID writer. This RFID writer can be the same RFID reader-writer that hospitals use to encode patient RFID wristbands. Alternatively, the present transceiver and processor in the custom controller box can do the programming via a touchscreen or other connected display, or take inputs from a cell phone via a WIFI or Bluetooth connection. The components in each sensor tag may be sandwiched and sealed in plastic. RFID radio frequency bands commonly used in ID and sensing vary from low (LF) to high (HF) to very-high (VHF) to ultra-high (UHF). Lower frequency RFID devices include hotel key cards which use near-field communication (NFC) technology to unlock doors. Higher frequency RFID devices operate over longer distances but are known to be sensitive to and be attenuated by moisture. Note that resonance-based sensing is known to be affected by their installation environments, and require special design features to reject interferences.

In some embodiments, RFID tag sensors receive resonance RF signals from the external antenna, which in turn draws RF power from the transmitter in the controller box. The controller box may be programmed to supply only the minimal RF energy to enable clear communication between sensor mat and controller box in order to allay concerns regarding high radio frequency radiation exposure which has been associated with certain diseases and cancer abnormalities in the brain and endocrine tissues. Since embodiments of the bed monitor are designed to track anomalous conditions, powering a collection of RFID tags used as sensors can be intermittent in normal conditions, allowing for variable duty cycle powering routines in order to lower a patient's total RF radiation exposure.

In some embodiments, the use of a single RFID tag sensor can report the presence and signal strength level of the attribute under detection. Using the built-in identification (ID) capability of the RFID tag sensors, each sensor can be tracked by its embedded ID code. A plurality of sensors may thereby add spatial, temporal and pattern recognition capabilities. In this way, a map image of the patient's body above a collection of sensors can be assembled with affected sensors; the bigger the sensor array, the higher the resolution. In some embodiments, a moving image akin to an animated comic strip (cartoon) is also available with added timing (i.e., temporal) data. The composite data may form the basis of activity pattern recognition. The sensor mat can perform the patient body position tracking function in this manner.

Patients with medically induced or physiologically challenged conditions are not expected or allowed to move while being confined. Data from the sensor mat can report the patient's real-time body position to a memory module disposed within the control box. According to some embodiments, an algorithm resident within the memory of the control box may be used to compare those profiles to medically prohibited profiles and initiate an alarm notification when caregiver intervention is required.

In order to prevent falls, patients confined to ICU and ACU hospital beds should not exit their beds without assistance. In some embodiments, moving image profiles generated by RFID tag sensor arrays in the sensor mat may be used to signal or forecast an impending patient action to exit their bed. With a composite of moving images over time, a patient attempting to exit his/her hospital bed can be recognized as distinctive activity patterns which can be further refined with artificial intelligence algorithms (AI) parsing additional quantities of in-situ data. Redundant data and multivariate analyses may be used to confirm the probability of a patient's expected fall and thereby initiate an alarm notification for care personnel intervention.

In some embodiments, bed vacancy can be defined as the condition where all sensors report null readings, as would be the case when a patient is out of bed without medical permission. Detection of bed vacancy in a monitored bed may serve as a positive indication that the patient has left the bed unassisted with a high probability of an expected fall. In some embodiments, detected bed vacancy can generate an alarm notification.

Incontinence monitoring is essential for all patients confined to hospital beds who are not allowed or expected to move while confined for physiological or medical reasons. Unless urination or defecation is handled in other ways (such as catherization, colostomy bags, or bed pans on call), bed confined patients have to be treated as incontinent. An incontinent patient is normally fitted with a generic absorbent article, either lying on an absorbent underpad or wrapped in a diaper. With the absorbent article placed on the bedsheet in registration with sensor mat, the type of incontinence (urine or feces) and its progress in real time from sensor to sensor can be detected by a combination of RFID tag moisture, temperature, and discrete gas sensors. Incontinence detection can be implemented in a manner similar to what has already been described in the narrowest form in U.S. Pat. Nos. 10,251,783 and 9,649,930 according to some embodiments. Note that while the previous patents described the use of an RFID tag sensor mat in specific incontinence applications, the present subject matter details embodiments which are concerned with the comprehensive health and safety of patients while the patient is confined to a bed, of which incontinence is but one manifestation. The volume of urine voiding can be determined by the size of the diffusion spot on the absorbent article along with timing data. In some embodiments, an adjustable volume value may be used to determine the trigger level of a urinary incontinence alarm in the form of binary coded data sent from the control box to the hospital information system. In some embodiments, the volume value can be adjusted such that small volume urine voids, or leaks, will not trigger an alarm for an absorbent article change. In some embodiments, fecal incontinence may be detected by a dedicated Hydrogen Sulfide ($H_2S$) gas detector.

Figure 1B:
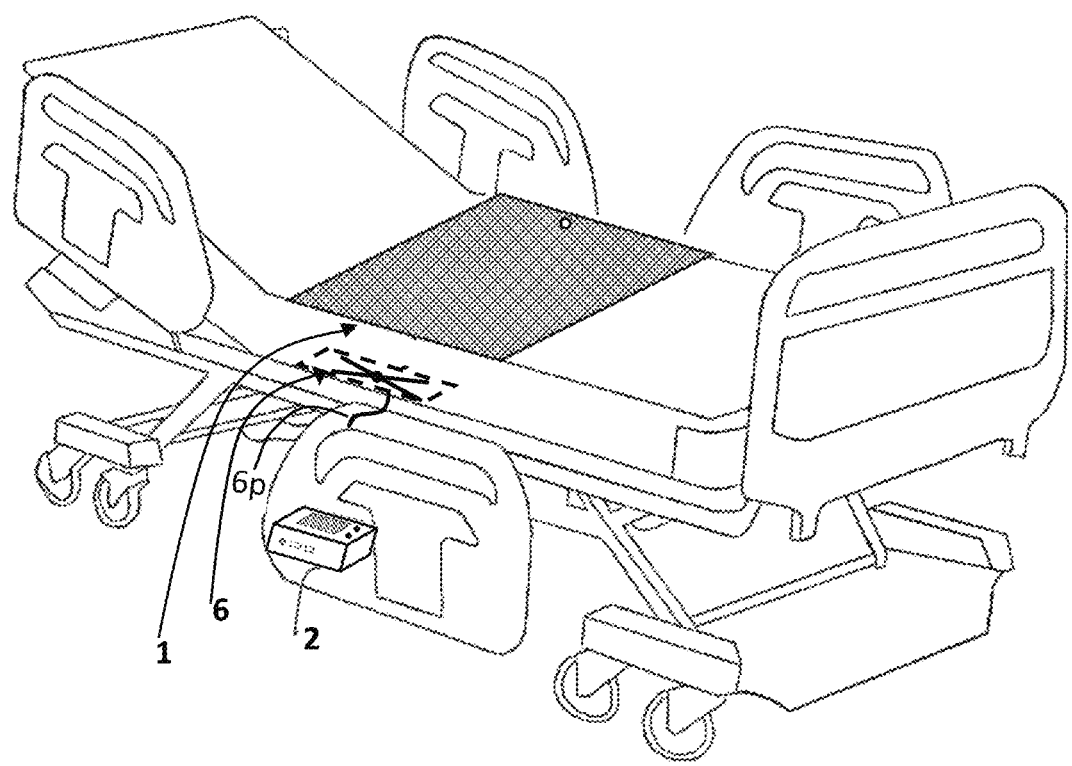
FIG. 1B is a perspective view of a bed monitoring system including a controller box and a sensor embedded mat that is wireless and positioned on a hospital bed mattress where the transceiver antenna is external and located below the mattress according to an embodiment of the present invention.

FIG. 1A is a perspective view of a bed monitoring system including a controller box 2 and a sensor embedded mat 1 positioned on a hospital bed mattress according to an embodiment of the present invention. During normal use, this sensor mat is hidden from view, being covered by an existing bedsheet upon which a patient resides. In some embodiments, sensor mat 1 is cleanable and reusable, fabricated using hospital grade polymer material that is soft and flexible. Sensor mat 1 may be sized to match a typical hospital-issue flat incontinence absorbent pad, most often spanning the width of the bed mattress. Alternate encapsulation methods can include natural rubber or plastic sheets which laminate the sensors. The sensors encapsulated in sensor mat 1 may be chosen to detect patient body conditions as well as other conditions that are germane to the goals of the bed monitor. The sensors can be wired or wireless according to various embodiments. In some embodiments, wired sensors cables may be bundled to exit on one side of sensor mat 1. For example, a pigtailed wire bundle 1p may connect to controller box 2 as illustrated in FIG. 1A. In some embodiments, sensor mat 1 may be completely wireless, utilizing wireless sensors adapted to communicate with controller box 2 through an antenna that has been embedded below the sensor arrays before encapsulation. In some embodiments, the antenna may be adhered to the bottom of finished wireless sensor mat 1. One advantage of this configuration is that it can reduce RF power transmission, while still retaining suitable beamwidth to cover the entire array. FIG. 1A and FIG. 1B also illustrate controller box 2, which may be placed within reach of care personnel along the periphery of the bed structure, for example, secured with quick release keyhole type hanger to a side safety rail as shown in this exemplary embodiment. In some embodiments, controller box 2 may include an external control panel and input/output receptacles, as well as an internal circuit board, power supply, processor, memory module (comprising controller software/instructions), and transceiver. Controller box 2 may include or connect with one or more output devices (e.g., display devices, speakers, printers etc.) according to some embodiments and as subsequently described in FIG. 8.

FIG. 1B is a perspective view of a bed monitoring system including a controller box and a sensor embedded mat is wireless and positioned on a hospital bed mattress where the transceiver antenna is external and located below the mattress according to an embodiment of the present invention. FIG. 1B is similar to FIG. 1A but different in a very important way. In this exemplary embodiment, sensor mat 1 is completely wireless. Passive RFID tag sensors embedded in sensor mat 1 connect to controller box 2 via transceiver antenna 6 located below the mattress or under the mattress support and in registration with sensor mat 1. Antenna 6 in this embodiment may require more RF power because of the distances involved, while beamwidth coverage of sensor mat 1 may be easier to achieve with natural RF signal divergence with distance. As shown in the figure, antenna 6 may connect to controller box 2 transceiver via its pigtail antenna cable 6p.

Figure 2:
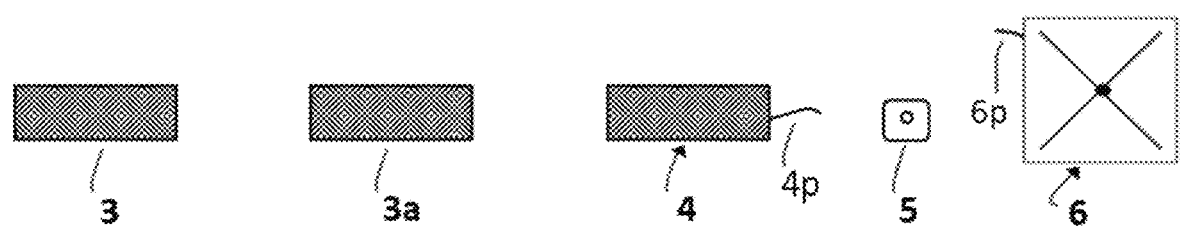
FIG. 2 is an illustration of selected components for installation in a sensor mat according to an embodiment of the present invention.

FIG. 2 is an illustration of selected components for installation in a sensor mat according to an embodiment of the present invention. Both passive and active RFID tag sensors are shown, along with a common antenna. In some embodiments, passive RFID tag sensors 3 are adapted to respond collectively to the same resonant frequency from an antenna. In other embodiments, a set of passive RFID tag sensors 3a are each adapted to respond to a different resonant frequency. In this manner, each passive sensor 3a in a group of like sensors may be individually and exclusively accessed. In some embodiments, each sensor 3a is field programable so as to respond to a different frequency than its intended neighbors. In some embodiments, active RFID tag sensors 4 may be used in the alternative. RFID tag sensor 4 may be wired to an external power source (e.g., a power supply or a battery) through its pigtail 4p for individual activation. Either type of RFID tag sensor may communicate via antenna 6, which transmits and receives data encoded in a resonant radio frequency.

Some embodiments may further include a gas sensor 5 communicatively coupled to the sensor mat for distinguishing between urinary and fecal incontinence based upon the detection of Hydrogen Sulfide ($H_2S$) gas. Sensor 5 can be RFID tag-based or discrete depending on availability and design goals. Antenna 6 may be a thin flat antenna communicatively coupled to the sensor tags. Some embodiments include a shielded antenna cable 6p extending from antenna 6 which may be used to connect to the transceiver disposed within controller box 2.

Radio frequency signal strength diminishes by distance and beamwidth from the point of origin. For accuracy, RFID tags are scanned in a serial manner. Commercial RFID handheld readers point at each RFID tag in a very close distance to read embedded ID information. Close distance reading allows for low RF powering and beamwidth focusing. RFID readers are technically RFID transceivers transmitting a specific radio frequency through a built-in antenna for activating a passive RFID tag and for receiving the ID signal transmitted from the same tag. Similarly, ID cards utilize similar technology where the ID card may be swiped across the reader in close proximity to the reading head. Reading applications at greater distances, such as garage gates and toll booths, ordinarily require higher power readers with directional antennas and/or high-power active RFID tags. Such applications still read data serially (i.e. one RFID tag at a time) within the bounds of the beamwidth of the antennas. RFID tags ordinarily upload embedded identification in a pulse-like manner. When this same reader is used to read a longer duration data transmission from a sensor tag among a set of proximately-situated sensor tags, it is important to minimize electromagnetic coupling between tags which result in cross sensitivity issues. Interference can degrade measurement accuracy and result in other adverse conditions. Resonance-based electromagnetic sensors are known to suffer from a variety of such environmental effects.

In some embodiments, a wireless sensor mat includes multiple passive RFID tag sensors 3 adapted to respond to a common resonance radio frequency when coupled to a singular transceiver antenna 6. Continuous recalibrations to known references may minimize potential spurious emissions (interference) from activated neighboring sensors as described above. Other embodiments are configured to power each tag individually. Embodiments which allow for individual activation of embedded RFID tag sensors 3a and 4 can thereby advantageously obtain clearer signals.

Figure 3:
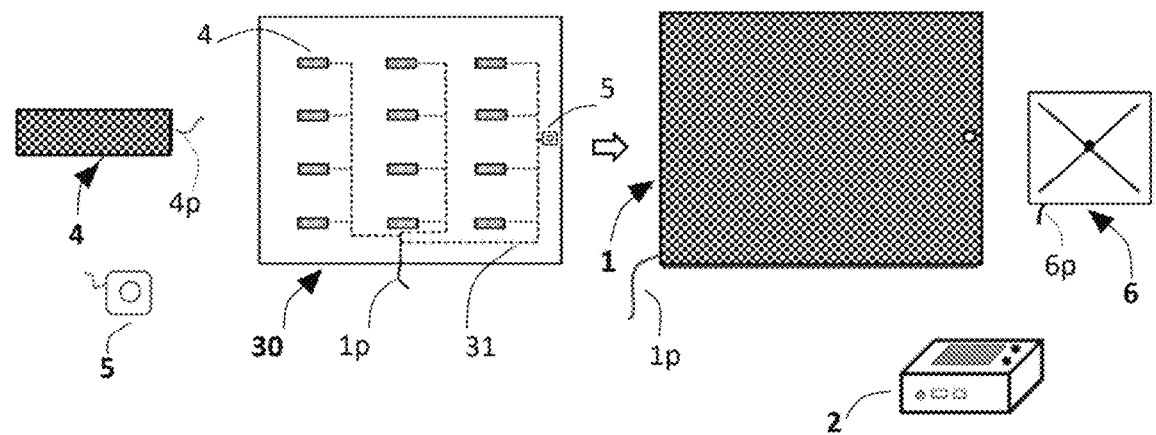
FIG. 3 is a top view of a components used in a 12-sensor embodiment configured to utilize active RFID sensors.

FIG. 3 is a top view of components used in a 12-sensor embodiment. Other embodiments with more or fewer components may be utilized depending on application needs. Each of the embodiments described here are configured to utilize active RFID sensors. Sensor 4 may be activated by power applied to its pigtail 4p. Importantly, each active RFID tag sensor 4 is powered individually to avoid interference from neighboring like sensors. Sensor mat 30 has parallel wires from active sensor 4 baled into bundle 31 to exit at pigtail 1p. Gas sensor 5 may be located close to one of the shorter sensor mat sides corresponding to the two sides of the bed, or alternatively, at mid bottom of the sensor mat 30. In some embodiments, gas sensor 5 sensing window is not encapsulated and is visible in finished sensor mat 1. Antenna 6 may be adhered to the bottom center of mat 1 to shuttle data between sensor tags 4 and controller box 2. Alternatively, antenna 6 can be encapsulated as the bottom part of mat 1 as in FIG. 1A. Antenna 6 can also reside below the mattress or below the bed frame as in FIG. 1B. Myriad other possible configurations and positions of the antenna are also contemplated in accordance with the scope of the present invention.

Figure 4A:
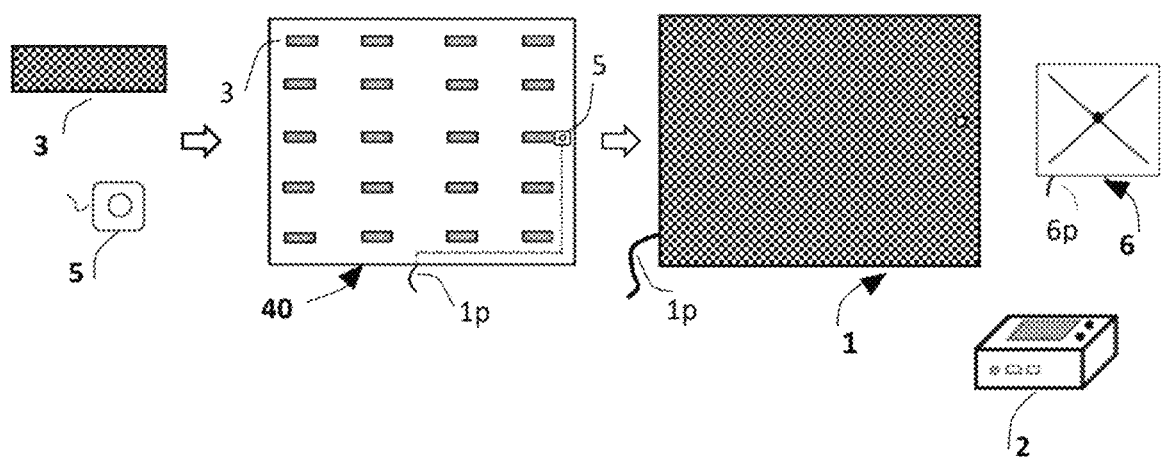
FIG. 4A is a top view of components used in a 20-sensor embodiment configured to utilize passive RFID sensors.
Figure 4B:
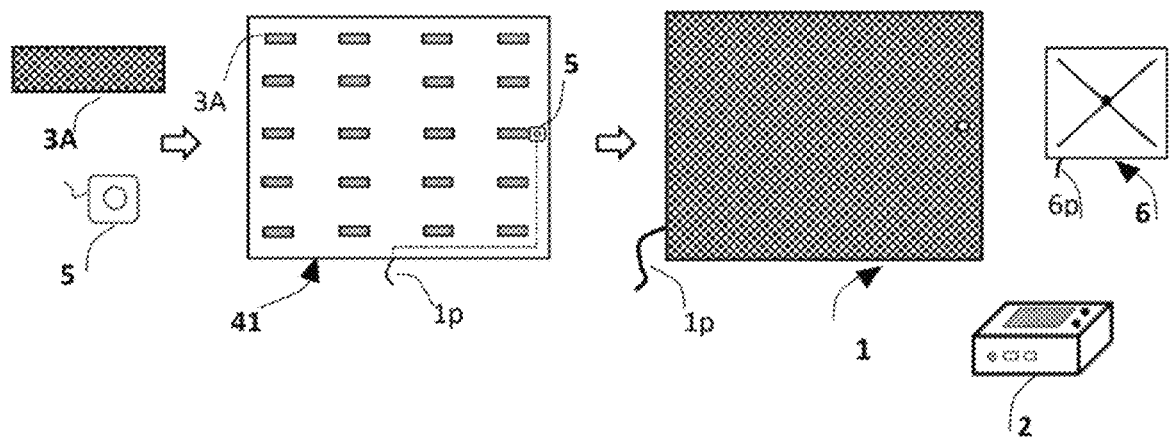
FIG. 4B is a top view of components used in a 20-sensor embodiment configured to utilize passive RFID sensors, wherein each sensor can be individually activated.

FIGS. 4A and 4B are top views of components used in a 20-sensor embodiment. Note that while twenty-tag embodiments are depicted in these figures, additional sensors can be used for even greater positional and temporal resolution. Conversely, to yield a more simplified, economical sensor mat, fewer sensors may be used. For example, a bare-bone four-tag sensor version with cartesian north-east-south-west layout can still provide position and temporal body sensing.

FIG. 4A depicts a 20-sensor embodiment in respective sensor layout 40 where all RFID sensor tag 3s are resonant to a single frequency and are turned on simultaneously. The finished sensor mat 1 may be completely wireless, adapted to connect with the transceiver in controller box 2 via antenna 6 located below mat 1. Note that although the embodiments depict a wireless sensor mat 1 featuring 20 sensors, sensor mats having different sensor configurations or featuring a different number of sensors can be used in the alternative according to embodiments of the present invention.

Sensor mat 1 connects to controller box 2 along with the cable 6p from antenna 6 if antenna 6 is embedded or attached below each sensor array. An external, higher power antenna 6 will have its antenna coaxial cable connect separately to controller box 2 when it is located below the mattress or under the mattress support. Each tag sensor 3 may be powered by a resonant radio frequency from antenna 6 thereby charging its power storage capacitor. In the embodiments depicted in FIG. 4A, all sensors are configured to activate simultaneously by the same resonant RF signal from antenna 6. In these situations, controller box 2 may address each RFID sensor tag 3 to read its contents before moving on to the next. Conversely, in the embodiment depicted in FIG. 4B, each passive RFID tag sensor is configured to activate individually in order to avoid RF interference generated by other RFID tag sensors.

FIG. 4B shows a similar 20 sensor design as depicted in FIG. 4A. However, according to various embodiments, sensor mat design 41 employs passive sensor tags that may use a different resonant frequency to allow for individual activation. This may require as many different frequency sensor batches to match each sensor mat sensor array (2,4,8,16,20,40 etc.). Efficiently, the RFIC (integrated circuit chip) in each passive RFID tag sensor 3A can be field programmed to respond to a different resonant frequency according to various embodiments. Field programming can be done using a suitably equipped and configured controller 2. Thus, the embodiments depicted in FIG. 4B may utilize a collection of variable radio frequency passive RFID sensors 3A encapsulated to form wireless sensor mat 1. Conveniently, this wireless 20-sensor mat 1 can be swapped with another wireless sensor mat with a different layout.

If it is desirable to distinguish between urinary incontinence discharges and fecal incontinence discharges, a gas sensor 5 may be optionally provided (as shown in FIG. 4A, layout 40 and FIG. 4B, layout 41) according to various embodiments. The gas sensor 5 may be adapted to connect to controller box 2 via sensor mat 1 pigtail 1p. Antenna cable 6p from antenna 6 may be adapted to connect to the controller box 2 transceiver. A processor in controller box 2 can select the correct radio frequency for the transceiver section to access the correspondingly resonant RFID tag sensor. Essentially, each sensor may be scanned serially with a unique resonant frequency so as to obtain respective sensory data.

Figure 5:
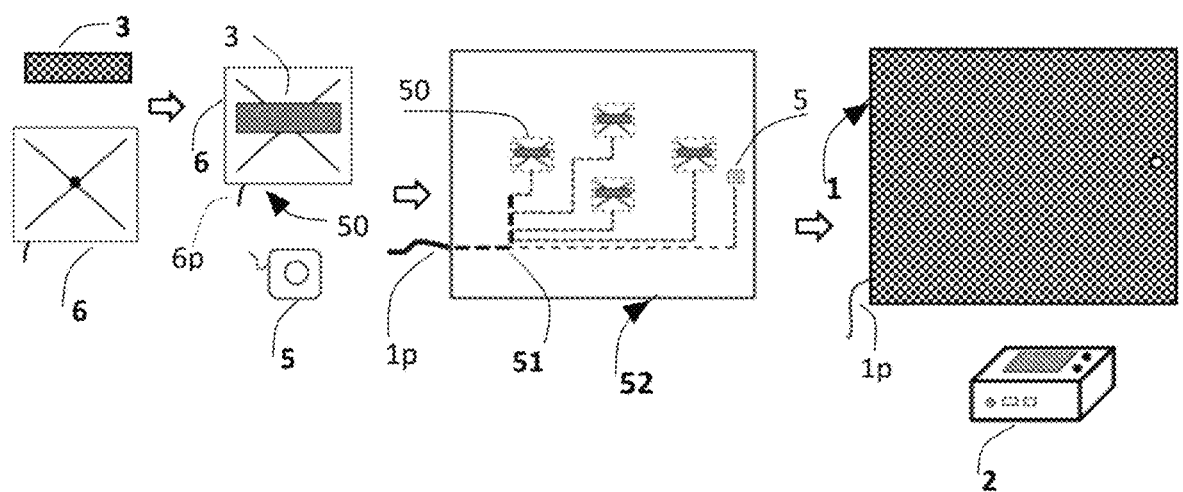
FIG. 5 is a top view of components used in a 4-sensor embodiment configured to utilize passive RFID sensors, each sensor being positioned upon a corresponding antenna.

FIG. 5 is a top view of components used in a 4-sensor embodiment configured to utilize passive RFID sensors. Each sensor is positioned upon a corresponding antenna. According to various embodiments, each antenna 6 may be an encapsulated thin PCB-thick design with its longer side matching RFID sensor tag 3 length. The two components together are designated as RFID sensor module 50 according to various embodiments, and may be encapsulated as part of sensor pad 1. Sensor module 50 may be activated by and communicate through its embedded antenna 6. In some embodiments, antenna cable 6p from all modules may form cable bundle 51 which exits sensor mat 1 as pigtail 1p to be connected to controller box 2. Sensor module 50 can sense moisture, temperature, and other environmental parameters depending upon selection of the type of RFID tag sensor 3. Each passive RFID sensor tag 3 can be turned on individually by powering the specific antenna 6 in each sensor module, with the finished sensor module 50 functioning much like those active or individually addressable passive RFID tag sensor 4 and 3A described in FIGS. 2, 3, and 4B so as to avoid interference from neighboring tag sensors.

In some embodiments, antenna 6 in each sensor module may be directional to focus a narrow beamwidth radio signal to its host passive sensor tag 3. Each sensor module can be shielded on its bottom and sides to further minimize stray resonant radio frequency from activating neighboring modules. Some embodiments are configured to utilize low RF power between antenna 6 and sensor tag 3 internal antenna to alleviate health concerns associated with high frequency and ultra-high frequency RFID transmissions. The closer the RFID tag sensor is to the transceiver antenna, the less power is required since RF power decreases by the square of distance.

Design 52 of FIG. 5 is an illustrative layout of four modules arranged in cartesian north-east-south-west manner with gas sensor 5 placed close to one of the short sides. This embodiment can provide a spatial map of the body above, whether the patient is lying flat, turned to the right, or turned to the left as well as detect the patient's incontinence emissions. This design can also include a Hydrogen Sulfide ($H_2S$) gas sensor for distinguishing fecal from urinary incontinence.

Figure 6A:
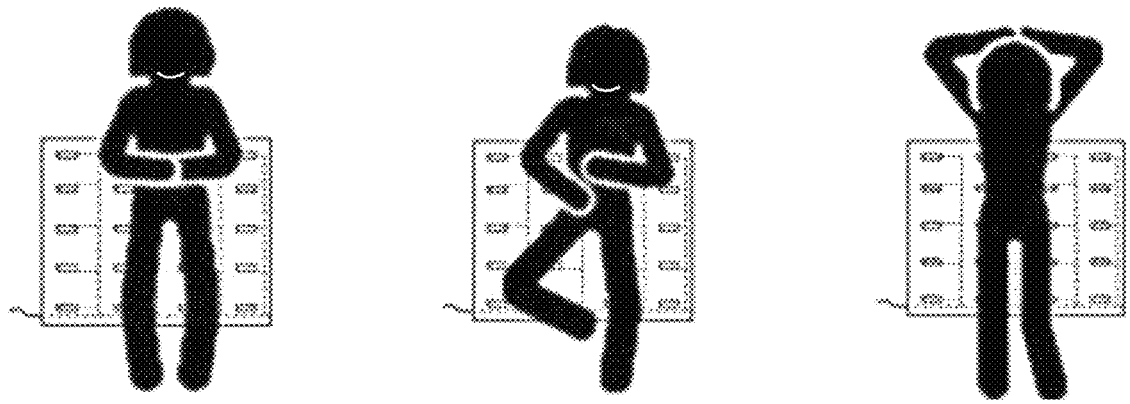
FIG. 6A is a top view of an exemplary sensor mat with a patient lying or sitting up in selected poses.
Figure 6B:
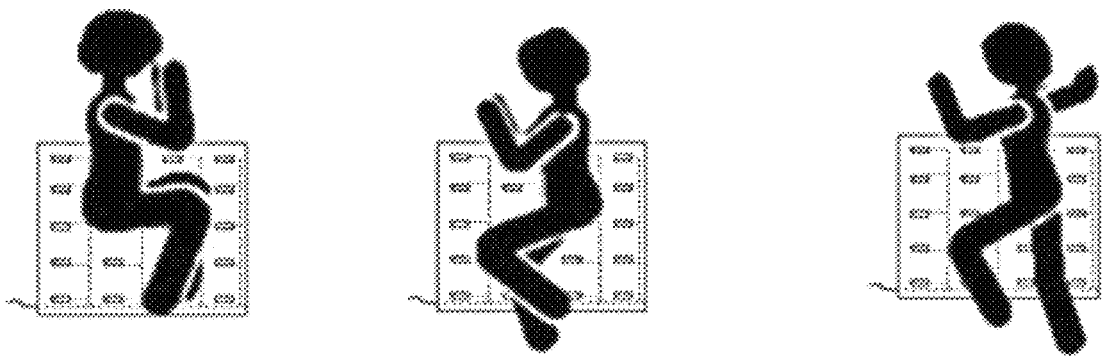
FIG. 6B is a top view of an exemplary sensor mat with a patient lying on its side in selected poses.

FIG. 6A is a top view of an exemplary sensor mat with a patient lying or sitting up in selected poses, while FIG. 6B depicts a patient lying on its side in selected poses. Using a binary yes/no response that is determinative of which sensor in the sensor mat is covered by the patient body part, the processor in controller box 2 can construct data sets (patterns) equivalent to coarse pixel images of body positions. Each of the poses of the avatar of FIG. 6A depicts the lower half of a patient on top of the sensor mat in supine or prone positions. In some embodiments, a three-dimensional image is available. By virtue of the ability of each RFID moisture sensor to report signal strength, a finer granularity of body contours (such as the extra pressure from the patient posterior versus the hollow of the back or tapering of the waistline) can be resolved.

Figure 6C:
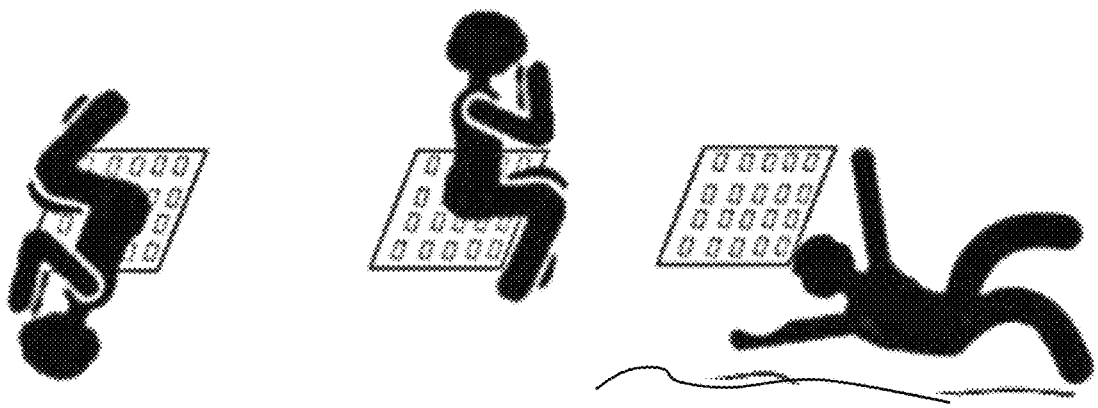
FIG. 6C is an illustration of a patient in the process of attempting to get out of their bed, but falling.

FIG. 6C depicts a sleeping patient attempting to sit up to exit bed. The left pane depicts the avatar positioning its legs to propel the body to sit up, the center pane depicts the avatar sitting up on the bed and turned left, with its legs hanging off this side of the bed (rail lowered), and the right pane depicts the avatar falling to the ground. In the left and center panes, the avatar will be lifting its body up and its posterior off the bed in a time sequence to be captured by signal changes in the sensors. Other maneuvers such as rolling to exit bed can similarly be captured. According to various embodiments, activity data patterns that represent bed exit activity and imminent fall danger may initiate one or more alarm notifications for hospital care personnel intervention. In some embodiments, the detected body movements in FIG. 6C and the detected body positions (if at least one body position was medically prohibited) may trigger separate alarms concurrently. In some embodiments, artificial intelligence (AI) algorithms may process captured in-situ data patterns relating to the actions of multiple patients rolling, rising and exiting bed, and refine the alarm triggering algorithms accordingly.

Figure 7A:
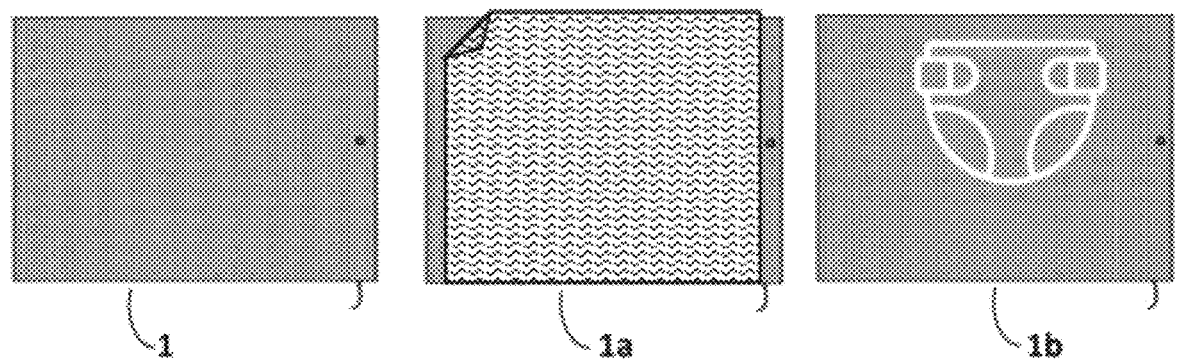
FIG. 7A is an illustration of an exemplary bed monitor sensor mat configured for urinary and fecal incontinence monitoring according to an embodiment of the present invention.
Figure 7B:
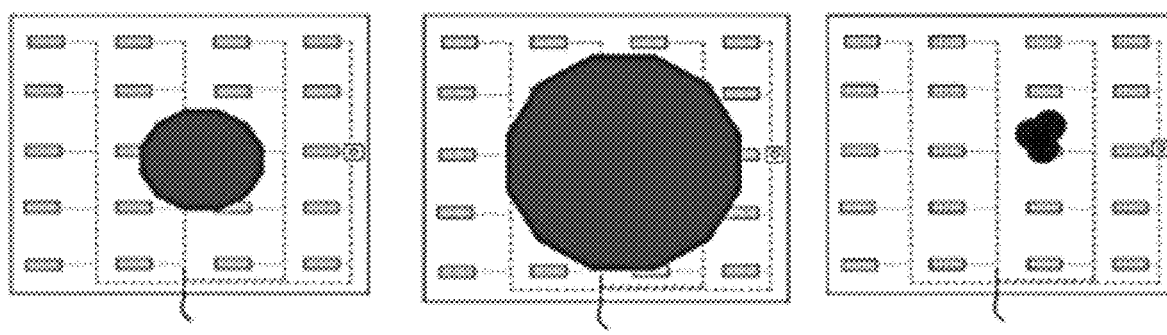
FIG. 7B is an illustration of various urinary and fecal incontinence events on an absorbent underpad in registration with the exemplary sensor mat depicted in FIG. 7A.

FIG. 7A is an illustration of an exemplary bed monitor sensor mat configured for urinary and fecal incontinence monitoring according to an embodiment of the present invention, while FIG. 7B is an illustration of various urinary and fecal incontinence events on an absorbent underpad in registration with the exemplary sensor mat depicted in FIG. 7A. Note that patients confined to their bed are ordinarily treated as incontinent patients by virtue of the fact that they are not allowed to leave their beds. Finished sensor 1 in FIG. 7A can monitor incontinence events in addition to sleep position and fall anticipation. In situations where a patient is known to be incontinent, an absorbent pad is frequently deployed, whether being wrapped around the patient or placed below the patient's posterior. In some embodiments, sensor mat 1 is able to detect incontinence events without requiring direct contact with any incontinence discharges. The absorbent underpad may be placed in registration with sensor mat 1 in FIG. 7A on top of the bedsheet (not shown), center pane 1a. Note that in some embodiments, the underpad does not cover the gas sensor 5 sensing window to allow for fecal gas Hydrogen Sulfide ($H_2S$) detection. In some embodiments, an absorbent pad placed on top of the bedsheet will not affect sensor mat 1 sensing capability. FIG. 7A right pane 1b shows a scenario where the absorbent pad is a diaper.

FIG. 7B depicts two incontinence incidents occurring on the absorbent pad (not shown, bed sheet below also not shown)—urinary incontinence and fecal incontinence. The left and center panes depict an incontinence event where a volume of urine is voided and then spread out due to diffusion effects in the absorbent material. According to various embodiments, urinary spread and diffusion rate can be mapped by responding sensors from under the diffusing spot. Urinary volume may be measured by a wet spot footprint and confirmed by rate data. When a specified threshold (e.g., from a typical 300 ml urine discharge) is reached, an alarm can be triggered for hospital care personnel to replace the wet absorbent pad. If temperature sensing is also available, such data can serve as a redundant check for positive urinary incontinence where temperature rise (just after discharge), and decay (after discharge and diffusion starts) over distance from the origin is evident. The right pane of FIG. 7B depicts a fecal incontinence event. Feces detection from discrete sensor 5 may be combined with location data from the affected RFID moisture and temperature sensors readings according to various embodiments.

Note that Hydrogen Sulfide ($H_2S$) gas is a distinctive characteristic associated with fecal presence.

Figure 8:
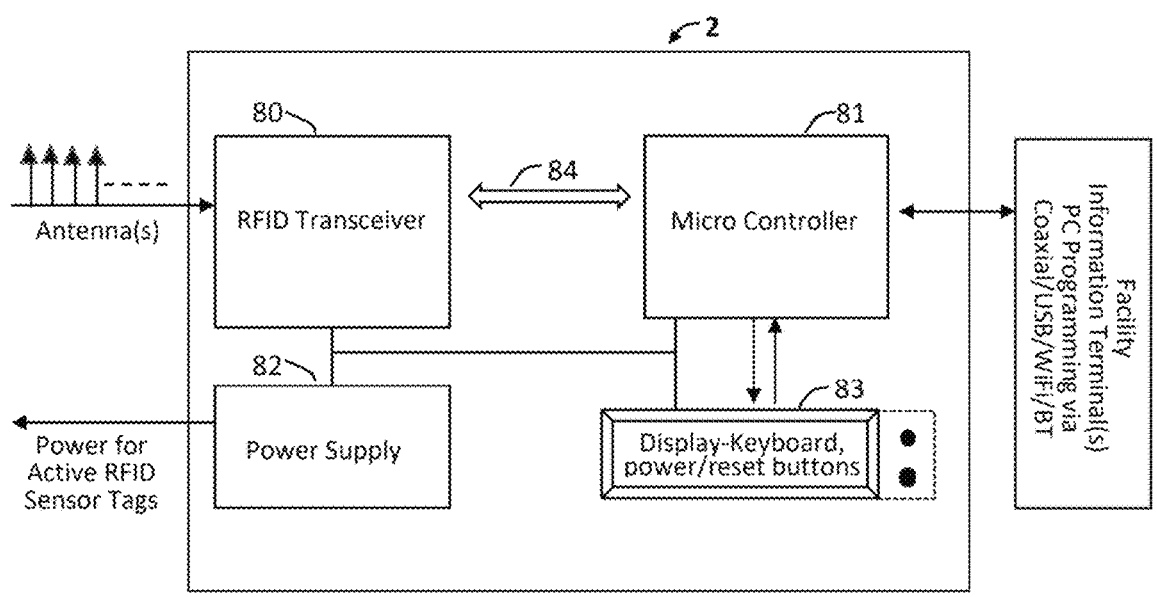
FIG. 8 is a block diagram of an exemplary controller box and its interconnections.

FIG. 8 is a block diagram of controller box 2. Major components include a RFID transceiver, a microcontroller with auxiliary functional circuitries to include I/O, volatile and nonvolatile memories switches, etc. as required. RFID transceiver 80 transmits, receives codes and decodes all signals into and out of compatible RFID sensor tags via antenna 6. Depending on the embodiment design, there can be a singular or multiple antenna 6s (see FIG. 3-5). RFID transceiver 80, in turn, receives commands from microcontroller 81 for transmit, receive, frequency choice, RF power output and read-write instructions via an exemplary GPIO bus 84. Data received by RFID transceiver 80 is then sent to microcontroller 81 via the same bus 84 for storage and processing based on application program(s) loaded onto its non-volatile memory via an external input from a PC, the facility information system or other suitable wired or wireless devices. The application program contains profiles to compare to information from the RFID tag sensors for action. There is also a dedicated combination display-keyboard or touchscreen 83 with hard buttons. Hard buttons are limited to on/off and reset to minimize emergency response confusion. Power supply 82 provides power for these components in addition to supply power to embodiments with active RFID sensor tags.

FIG. 9 is a schematic of an exemplary bed monitoring system in relation to a Hospital Information System (HIS) according to an embodiment of the present invention. According to various embodiments, controller box 2 input-output receptacles may be located at one of the sides. AC power input 91 can plug into the left receptacle, sensor mat 1 and power (for active FIG. 3 RFID tag sensor 4) and antenna 6 cable(s) may plug into the center, while bed monitor data output exits from the right receptacle to be connected to the hospital information system (HIS) 90. HIS terminations can typically be tapped in each hospital room on the hospital bed end panels or on a wall. Alternatively, controller box 2 can connect to HIS wirelessly according to various embodiments. When controller box 2 is programmed with alarm trigger levels, this bed monitor can issue redundancy checked alarm signal notifications for body turning, prohibited body poses, fall anticipation, bed vacancy, and incontinence. In some embodiments, all setup and programming can be done on the controller box 2 touch display. The controller box 2 touch display may be may be disposed upon a side of controller box 2, or may be a remote touch display in other embodiments. According some embodiments, setup and programming can be done via an app resident on a user's smartphone, tablet, or other such computing device.

In some embodiments, when alarms are generated, HIS may notify care personnel via nurse station screens, smartphones, or proprietary devices such as beepers. In some embodiments, each alarm signal can be set to persist until the alarm condition is reversed, such as when the patient is turned, the patient's prohibited body stance is corrected, the bed is reoccupied, or an absorbent pad changed. The time interval for care personnel remediation relative to each alarm can be automatically logged into the patient record for care evaluation by hospital or government auditors. Patient families can also receive real time or compiled scheduled service records routinely or as a hospital revenue item. HIS capabilities include data entry directly into patient records. This data may include, without limitation, care, equipment, and material usage billing according to various embodiments.

FIG. 10 is a table listing exemplary bed monitor functions, primary and fail-safe detection technologies, and the discriminating algorithms used to set alarm triggers according to an embodiment of the present invention. Column 1 lists exemplary functions which may be used to send notifications to care personnel when preset conditions are satisfied: (1) Body position, notification to turn patient when body position has not changed over a preset interval; (2) Body position resolution to detect body positions not medically permitted; (3) Impending Fall and Bed Vacancy monitoring to detect a pattern indicating a patient attempt to exit bed and possibly fall, along with bed vacancy verification; (4) Incontinence monitoring to detect urine and optionally, feces. Column 2 lists primary sensor enabling technology being moisture to detect the human body, and gas to distinguish feces incontinence. Column 3 lists redundant confirming sensor technology, such as temperature, to distinguish other moisture bearing objects from the human body or body waste, as both exhibit typical body temperature characteristics. Column 4 lists collective sensor outputs that can be used to reject false positive or negative triggers. Sensor level (parameter), location (spatial), timing (temporal) and set (pattern) may all be considered before an alarm is set according to embodiments of the present invention. In some embodiments, artificial intelligence (AI) algorithms can refine data gathered from actual hospital situations.

Figure 11A:
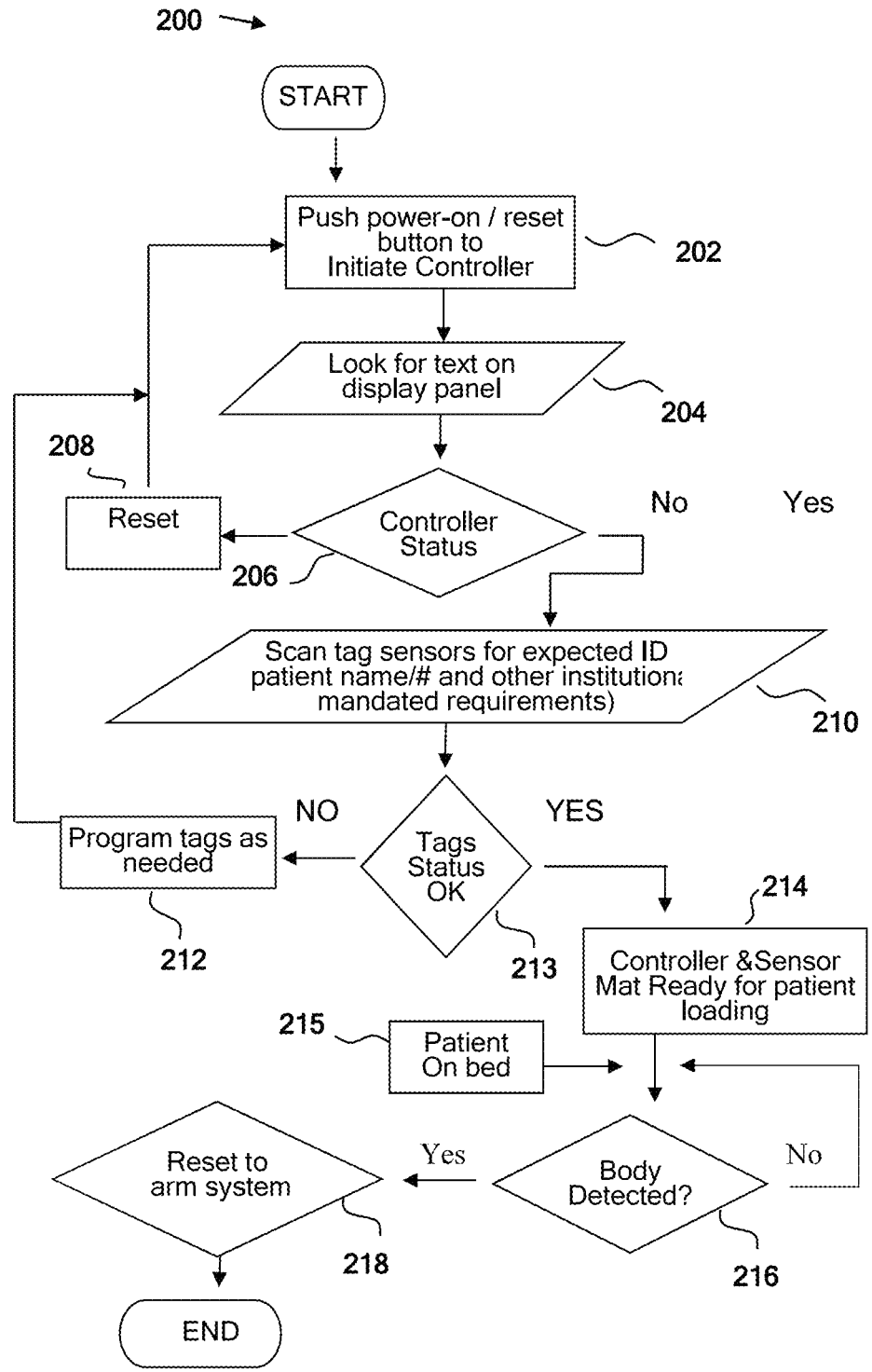
FIG. 11A is flow chart of an exemplary bed monitor system initiation according to an embodiment of the present invention.

FIG. 11A is a flow chart 200 for an exemplary bed monitor initiation routine according to an embodiment of the present invention. Assuming that sensor mat 1 is positioned on the bed below the bed sheet and centered to the intended patient posterior, antenna 6 may be located appropriately according to patient height in relation to the head of the mattress. Cables from sensor mat 1 (as well as from a separate external antenna 6 in some embodiments) may be connected to controller box 2. The set-up process may begin with the power being switched on at block 202. The system's response may be indicated by a display panel response at block 204 indicating the controller's status at block 206. In some embodiments, the RFID tag sensor ID may appear onscreen in a customer (hospital, institution, or personal) specified format with a unique ID 210 for each RFID tag sensor. An ID can include, without limitation, patient name, room number, and hospital record number—if so programmed. At block 212, changes can be made to any or all RFID tag sensors by using the touchscreen keyboard and accessing a screen code for ID programming according to onscreen instructions. In some embodiments, the system is operational at block 214 when all conditions for initiation are met, whereupon a patient is introduced into the bed (at block 215) with his/her bottom in registration with sensor mat 1 and upon system reset. Bed monitoring may begin when the controller detects a body at block 216 and displays a normal bed monitor activation status (at block 218) after the reset button is pushed.

Intended application of incontinence monitoring may also utilize a set-up procedure for initiation according to some embodiments. Each institution is likely to utilize a different brand and absorbency of absorbent pad. Thus, according to some embodiments, absorbency information can be input into the system in order to determine incontinence alarm levels. Assuming that only one brand and type of absorbent pad is used, this may be a one-time setup procedure with each institution. In some embodiments, the set-up procedure for the user may involve applying a specified amount of water to the center of the absorbent pad in registration with sensor pad 1, and then pressing a button when the system is set to the absorbent pad setup mode.

Figure 11B:
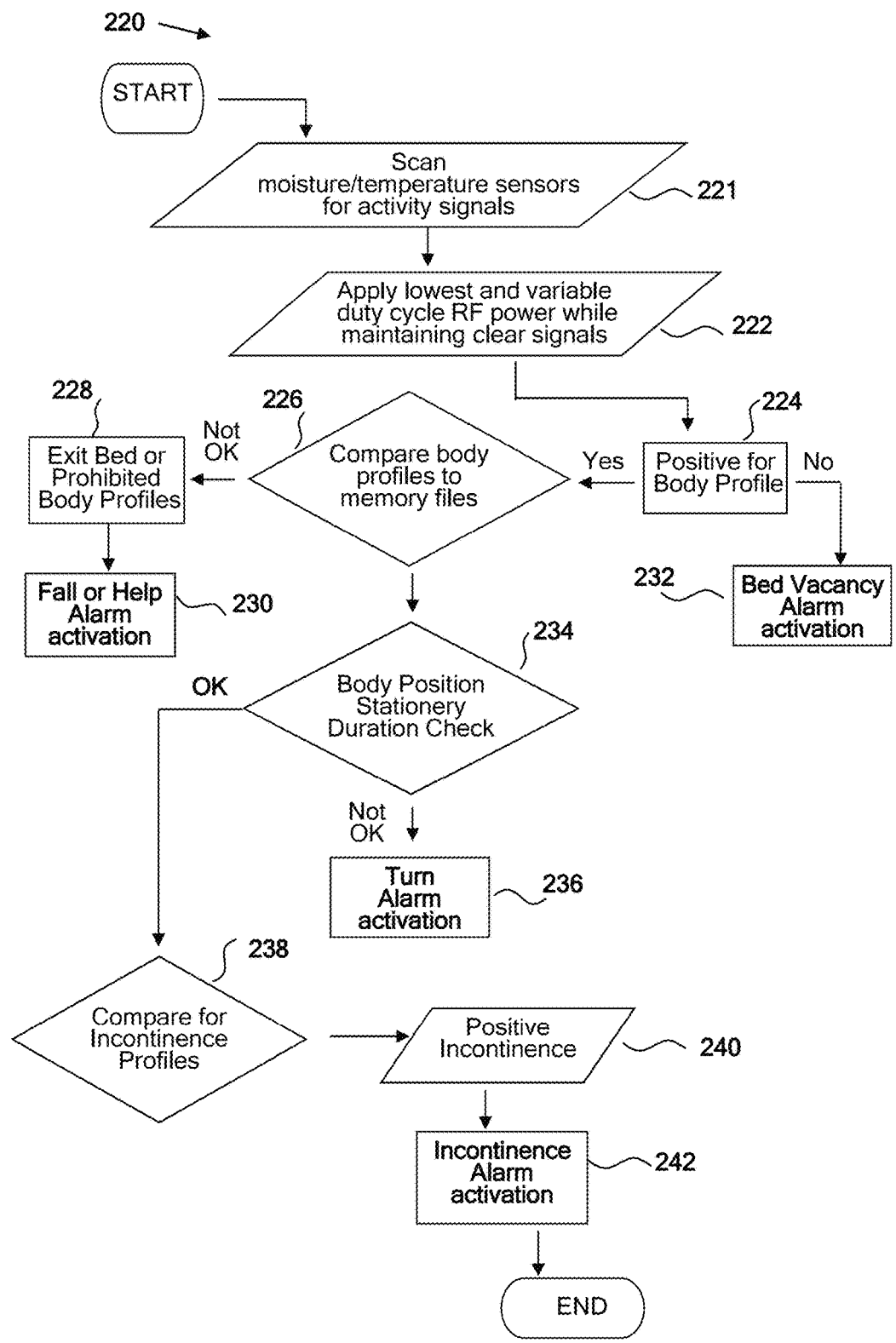
FIG. 11B is a flow chart of an exemplary system operation according to an embodiment of the present invention.

FIG. 11B is a flowchart 220 depicting an exemplary method for utilizing RFID tag sensors to detect and report anomalous patient conditions while the patient is bed-bound. At block 221, controller box 2 issues a command for the transceiver to scan embedded RFID tag sensors in sensor mat 1 for body and/or body effluence signals, from left or right by rows in a continuous loop. The lowest power is applied while maintaining clear signals, at that point variable duty cycle RF powering (at block 222) is applied and again clear signals confirmed. Each validated complete loop typically draws a pattern which may be compared to profiles stored in the microcontroller in order to determine whether a body is present at 224. If no human body is detected and verified according to, for example, the detection technologies described in FIG. 10 and confirming technologies such as moisture and temperature null status, bed vacancy alarm 232 is set to activate. If a body is detected, then the microprocessor, at block 226, may compare the detected body profile signals to stored memory reference profiles and determine at block 228 (again using the technologies described in FIG. 10) if the patient body exhibits prohibited body positions or whether there appears to be an impending bed exit attempt. A help or fall alarm 230 may be set upon confirmation. At block 234, if the patient body profile is stationery for a specified period of time (e.g., 2 hours), then at block 236, a turn alarm may be set after confirmation. At block 238, an exemplary incontinence detection with elevated RFID tag sensor moisture and temperature sensor codes (see FIG. 12) compares incontinence and body profiles to stored reference data, and if positive (block 240), will trigger an incontinence alarm at 242. Note that exemplary software with redundant physical and attribute sensors along with special, temporal, and set data (FIG. 10) may minimize false positive and false negative determinations according to some embodiments.

Figure 12A:
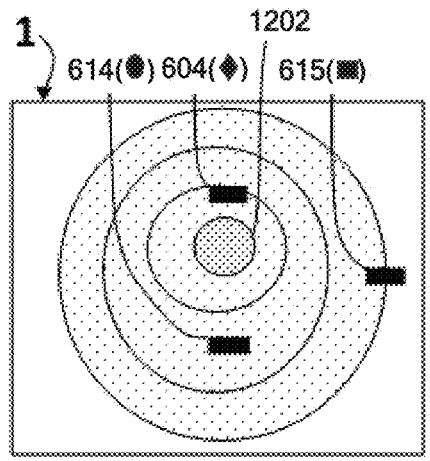
FIG. 12A is a top view of an exemplary sensor mat configured for demonstration of bed monitor system reacting to environmental stimulus.

FIG. 12A illustrates an exemplary moisture diffusion, incontinence simulation situation using a 3-sensor design with three passive RFID tag sensors embedded in sensor pad 1. 200 ml of water is poured into an absorbent pad with registration to sensor mat 1 below. Specifically, passive RFID tag sensor with ID 604 is the locus of a typical body hip or tail bone with the body facing sensor 614, according to patient height in relation to the head of the mattress. The target incontinence effluence point, circle 1202, is the initial wet spot which grows outward to cover passive RFID tag sensor 614. This volume of water diffuses outward towards RFID tag sensor 615 to completely saturate the underpad. Conveniently, all three passive RFID tag sensors can detect moisture as well as temperature.

Figure 12B:
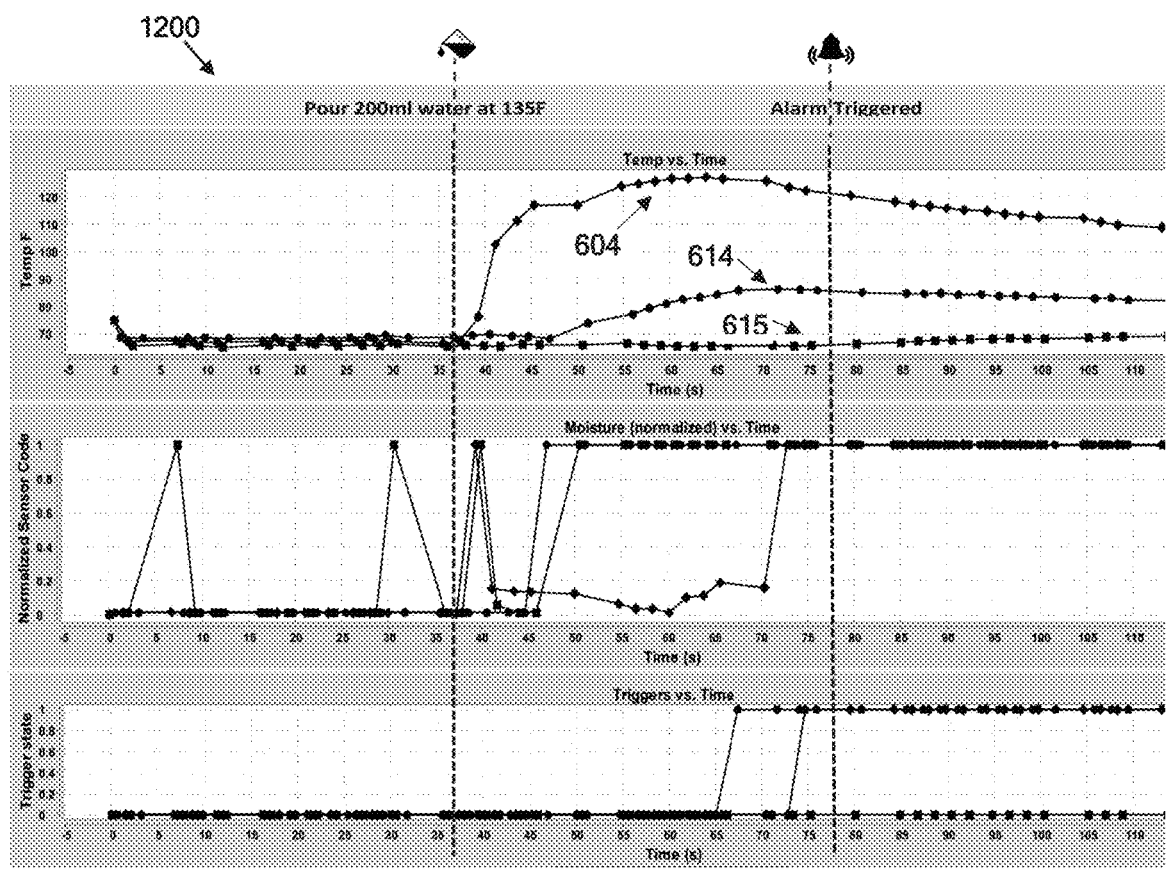
FIG. 12B is a sample graph of FIG. 12A exemplary bed monitoring system reaction to urine incontinence according to an embodiment of the present invention.

FIG. 12B is a RFID tag sensor output data graph 1200 recording the simulation of FIG. 12A. 604, 614 and 615 are RFID tag sensor IDs detected to be reporting. The graph starts at time zero and 200 ml 135 F warm water is introduced at 35 seconds. The top graph is temperature, and shows a baseline temperature of about 68 F ambient, then a risetime of 32 seconds to 126F before cooling down. The warmest location is at RFID tag sensor 614 where the 135F water is sourced, and cooling as the wet spot spreads outward towards 604 and then 615. The middle graph is moisture, which shows the sensor code response to the diffusion of water from source location 614 of FIG. 12A and continues outward to cover 604 and 615 within 53 seconds. Note that occasional sensor spikes such as at 4 to 9 seconds and 28 to 36 sec, etc. are typical of RF resonance data and ignored by the alarm triggering (bottom graph) algorithm (note that the display can be further filtered for a cleaner display reading if desired). Alarm triggering is set at 75 seconds after fail-safe algorithms have verified that threshold volume effluence is reached, temperature rise and decay is typical of urine incontinence (rather than, for example, a drinking water spill) and moisture sensor codes rise meets set parameters. This exemplary demonstration of RFID tag sensor response to a simulated incontinence scenario uses only temperature and moisture sensors, additional environmental sensors can make the system even more discriminant and tolerant of false negative or false positive alarm triggering.

Figure 13A:
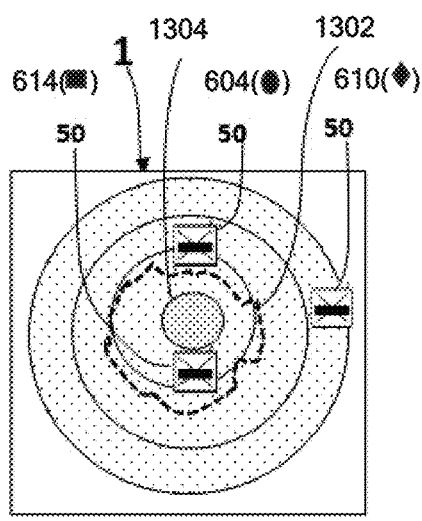
FIG. 13A is a top view of an exemplary sensor mat configured for demonstration of bed monitor system reacting to environmental stimulus.

FIG. 13A illustrates an exemplary bed occupancy situation coupled with an incontinence event. The scenario begins with an underpad on top of the bed sheet in registration with sensor mat 1. This sensor mat 1 design is an embodiment of sensor mat construction described in FIG. 5 with 3 sensor modules 50. Each module 50 here is represented by 604 or 614 or 610, the IDs of the RFID tag sensors of the FIG. 13B data graph. The body in contact with mat 1 is represented by outline area 1302. Incontinence occurs underneath patient bottom profile 1302 at location 1304 (circled), simulated by injecting 100 ml of 98F water through a tube. From 1304 the incontinence effluence spreads out in concentric circles to cover the entirety of the underpad.

Figure 13B:
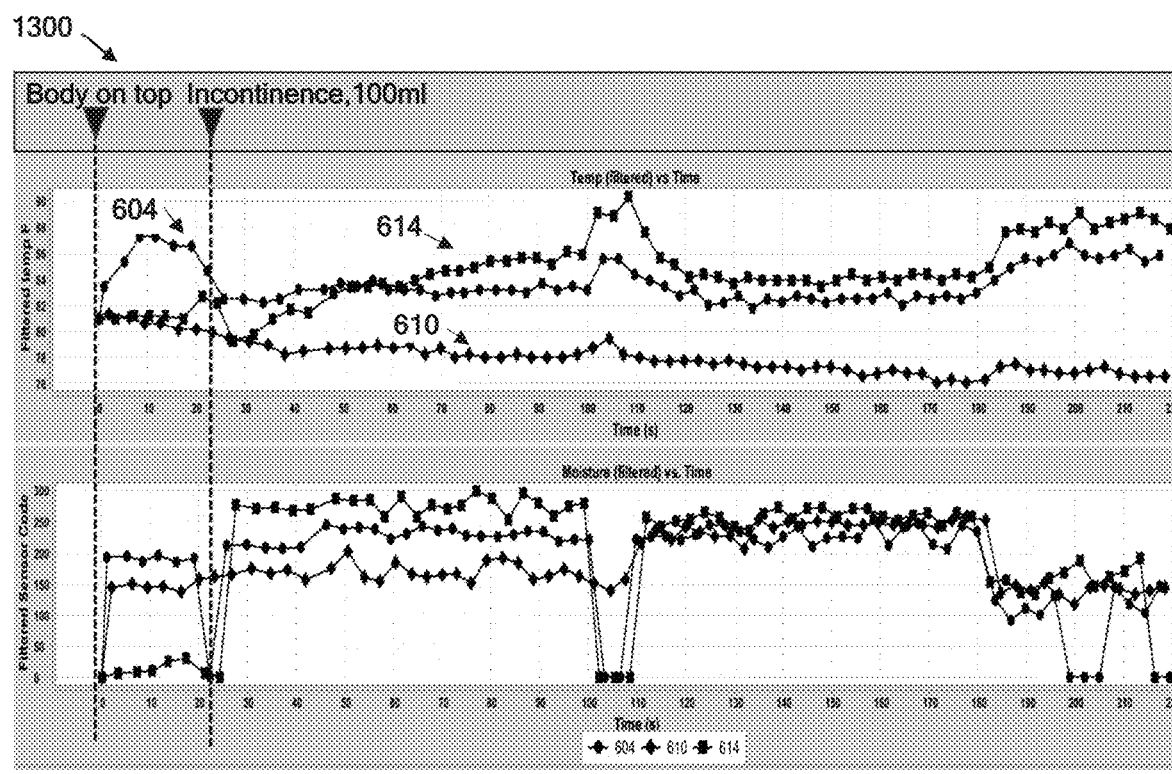
FIG. 13B is a sample graph of FIG. 13A exemplary bed monitoring system in a normal bed occupancy scenario according to an embodiment of the present invention.

FIG. 13B is the RFID tag sensor data graph 1300 recording the situation of FIG. 13A. The graph starts at time zero with a body lowered onto an underpad as described in FIG. 13A so as to trigger the temperature and moisture responses of top and bottom graphs. In an operating environment, the graphs would start at time 18 seconds where sensor mat 1 responds to a dry body in a steady state situation whereby the temperature graphs would show body temperature response to the lower body covered location 1302 (FIG. 13A) and RFID sensor modules corresponding to tag sensors 604 and 614. Moisture response on bottom graph shows 614 at 200 sensor units and sensor 610 at 150 sensor units because human body is 60% moisture (here sensor 604 is not responding due to the pressure on the protruding body bottom directly on top). At 22 seconds, incontinence occurs. The temperature shows sensor modules 604 and 614 responding to the rise and decay of the body fluid spreading out from the point of effluence while 610 is farther away but still shows the cooling effect. All three sensor modules on the bottom moisture graph show heightened sensor code due to the extra water response adding to the original body moisture. Note that sensors 614 and 604 respond at the time of incontinence but their moisture sensor codes show an anomalous reading at 98 seconds because of relaxation of the body pressure, probably a natural body response when wetness is sensed and a twitch or shift of body location. Pressure is resumed at 110 seconds, and at 180 seconds the patient twitches again.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims

What is claimed is:

1. A bed monitoring system comprising:
   a sensor mat configured to detect moisture independently from contact with a sensory surface, the sensor mat comprising:
   a plurality of RFID tag sensors, wherein each RFID tag sensor comprises an integrated circuit that is adapted to detect a temperature and that is further adapted to determine a moisture level based at least in part upon a detected level of RF attenuation, and an internal antenna that is adapted to be resonant with an external signal source; and a controller box comprising:
- a processor;
- a memory module communicatively coupled to the processor; and
- an RFID transceiver adapted to receive signals from RFID tag sensors;

wherein the memory module comprises a set of instructions which, when executed by the processor, generates a positional representation of a human body in relation to the sensor mat based at least in part upon temperatures and moisture levels associated with each RFID tag sensor of said plurality.

2. The system of claim 1, wherein the set of instructions further comprises instructions which, when executed by the processor, record a set of positional representations of said human body over a period of time.

3. The system of claim 2, wherein the set of instructions further comprises instructions which, when executed by the processor, generates an alarm when a positional representation has not changed over a designated interval of time.

4. The system of claim 2, wherein the set of instructions further comprises instructions which, when executed by the processor, resets a timer when a positional representation has changed over a designated interval of time.

5. The system of claim 2, wherein the set of instructions further comprises instructions which, when executed by the processor, generates an alarm when the set of positional representations substantially match a predetermined prohibited pattern.

6. The system of claim 2, wherein the set of instructions further comprises an artificial intelligence algorithm adapted to adjust at least a portion of said set of instructions based at least in part upon an analysis of recorded sets of positional representations.

7. The system of claim 1, wherein the set of instructions further comprises instructions which, when executed by the processor, determines whether a sensed region contains a human being, a human being undergoing an incontinence discharge, or an inanimate object, based at least in part upon determined moisture levels.

8. The system of claim 1, wherein the set of instructions further comprises instructions which, when executed by the processor, generates an alarm when a human body is not presently detected to be within a predetermined distance of the sensor mat.

9. The system of claim 8, wherein the set of instructions further comprises instructions which, when executed by the processor, tracks the onset and progress of incontinence effluence.

10. The system of claim 1, wherein the set of instructions further comprises instructions which, when executed by the processor, displays positional representations of a human body in real-time.

11. The system of claim 10, wherein displaying positional representations of a human body in real-time further comprises representing each RFID tag as a pixel with pixel brightness corresponding to temperature.

12. The system of claim 10, wherein displaying positional representations of a human body in real-time further comprises representing each RFID tag as a pixel with pixel brightness corresponding to moisture level.

13. The system of claim 1, wherein the set of instructions further comprises instructions which, when executed by the processor, directs the transceiver to use the minimal amount of RF power for enabling communication between the sensor mat and the controller box.

* * * * *